United States Patent [19]
Uchio et al.

[11] 3,993,543
[45] Nov. 23, 1976

[54] PROCESS FOR PRODUCING PYRUVIC ACID BY FERMENTATION

[75] Inventors: Ryosuke Uchio, Zushi; Kenji Kikuchi, Kawasaki; Hitoshi Enei, Zushi; Yoshio Hirose, Fujisawa, all of Japan

[73] Assignee: Ajinomoto Co., Inc., Tokyo, Japan

[22] Filed: July 7, 1975

[21] Appl. No.: 593,291

[30] Foreign Application Priority Data
July 8, 1974 Japan................................. 49-77960

[52] U.S. Cl.................................. 195/29; 195/30; 195/47
[51] Int. Cl.²........................................ C12D 13/06
[58] Field of Search................ 195/29, 30, 28 R, 47, 195/82

[56] References Cited
UNITED STATES PATENTS
3,616,218  10/1971  Shiro et al. ........................... 195/29

OTHER PUBLICATIONS
Chemical Abstracts, vol. 61, 11285a; 1964.

*Primary Examiner*—A. Louis Monacell
*Assistant Examiner*—Robert J. Warden
*Attorney, Agent, or Firm*—Cooper, Dunham, Clark, Griffin & Moran

[57] ABSTRACT

Improved method for producing pyruvic acid by fermentation of pyruvic acid producing mutants of the strain *Candida lipolytica* which require methionine and thiamine for growth.

5 Claims, No Drawings

PROCESS FOR PRODUCING PYRUVIC ACID BY FERMENTATION

This invention relates to a process for producing pyruvic acid by fermentation, and particularly to a process for producing pyruvic acid by fermentation of yeasts of the genus Candida.

Pyruvic acid is a valuable starting material for producing useful amino acids such as tryptophane, tyrosine or alanine by known methods. It is used by itself as a flavoring agent to impart a sour taste to foods.

It is known that yeasts of the genus Candida which require thiamine for growth, produce pyruvic acid in growth mediums (Journal of Biological Chemistry, Vol. 33, page 158, 1969). However, the yields are low, and consequently the procedure has not been adapted to commercial practice.

Thus, one of the objects of this invention is to provide an improved process for the production of pyruvic acid which overcomes the disadvantages and deficiencies of prior art methods.

Another object of the invention is to provide a process for producing pyruvic acid by fermentation which may be carried out in a facile manner.

A further object of the invention is to provide a process for producing pyruvic acid by fermentation which may be carried out advantageously on an industrial scale at low cost to give a high yield of the product.

It has now been discovered that remarkably improved yields of pyruvic acid may be obtained compared with the conventional methods, by culturing pyruvic acid producing mutants of the genus Candida which require thiamine and methionine for growth.

The methionine and thiamine requiring mutants are derived from the parent strains, which may or may not require thiamine for growth, by known mutagenic processes such as exposure to mutagenic doses of ionizing radiation (ultra-violet light, X-rays) or chemical agents (nitrous acid or N-methyl-N'-nitro-N-nitrosoguanidine) and thereafter screening the parent strains to select those mutants having the described properties.

An example of an effective pyruvic acid producing mutant derived by this process is Candida lipolytica AJ 14353 (FERM P-2628) and strains thereof. The microorganism, identified by FERM P-number, is available from the Fermentation Research Institute, Agency of Industrial Science & Technology, Chiba-shi, Chiba-ken, Japan.

The culture media in which the mutants of the invention produce pyruvic acid are largely conventional. They will contain sources of assimilable carbon, nitrogen, inorganic salts, vitamins and methionine. Suitable carbon sources include saccharides such as glucose, fructose, sucrose, starch hydrolysates; organic acids such as acetic acid, propionic acid a and alcohols such as methanol or ethanol. Several organic or inorganic nitrogen containing materials such as ammonium sulfate, ammonium nitrate, sodium nitrate, potassium nitrate, urea, peptone, meat extract, may be advantageously employed as nitrogen sources.

Such inorganic salts as $KH_2PO_4$, $K_2HPO_4$, $MgSO_4$, $MnSO_4$, and $FeSO_4$ may be used. It is not necessary to employ pure methionine and thiamine. Sources of methionine and thiamine such as their biologically transformable analogs, or compositions known to contain the amino acids such as yeast extract, corn steep liquor may be utilized.

During cultivation, the pH of the culture media is preferably held at from 3 to 8 using appropriate alkaline agents such as sodium or potassium hydroxide.

The fermentation is advantageously carried out at from 25° C to 35° C.

The pyruvic acid accumulated in the fermentation broth is recovered by conventional methods. One useful procedure is to remove the cells by filtration or centrifugation, acidify the broth, extract with ether, concentrate under reduced pressure, take up the residue in water, and crystallize by the addition of a miscible liquid such as an alkanol.

The following non-limiting examples are given by way of illustration only.

EXAMPLE 1

An aqueous medium having following composition with a pH of 5 was prepared.

| | |
|---|---|
| glucose | 10 % |
| $NH_4NO_3$ | 0.5 % |
| $KH_2PO_4$ | 0.2 % |
| $MgSO_4 . 7H_2O$ | 0.1 % |
| meat extract | 0.02% |
| thiamine HCl salt | 3 γ/l |
| $Fe^{++}$ | 2 p.p.m. |
| $Cu^{++}$ | 2 p.p.m. |

Two aliquots, each containing 15 ml of the aqueous medium were sterilized in separate 500 ml flasks, and each medium was supplemented with 3% sterilized $CaCO_3$.

Candida lipolytica AJ 4565 (parent strain requiring only thiamine) and Candida lipolytica AJ 14353 (FERM P-2628; mutant strain requiring both thiamine and methionine) were innoculated into the separate flasks. The flask containing Candida Lipolytica AJ 14353 was additionally supplemented with 0.03% of DL-methionine. The mediums were cultured with aerobic shaking at 30° C for 72 hours.

The amounts of pyruvic acid accumulated in the culture liquor were as follows:

| | | |
|---|---|---|
| Candida lipolytica | AJ 4565 | 25.7 mg/ml |
| Candida lipolytica | AJ 14353 | 43.6 mg/ml |

Pyruvic acid in the culture liquors was recovered by the following method:

Culture liquor

↓

Remove cells by centrifugation

↓

Adjust pH to less than 2.0

↓

Extract with ethyl ether

↓

Concentrate under reduced pressure at less than 45° C

↓

Take up residue in cool water

Adjust pH to 6.0

↓

Add ethanol to precipitate desired product

EXAMPLE 2

Cultivation was carried out with same strains and in the same mediums and under the same conditions as described in Example 1, except that 2% of propionic acid or ethanol were used in the culture medium instead of glucose.

The amounts of pyruvic acid accumulated in the culture liquor were as follows:

| microorganism used | carbon source | pyruvic acid accumulated (mg/ml) |
|---|---|---|
| Candida lipolytica AJ4565 | propionic acid ethanol | 0.8 1.3 |
| Candida lipolytica AJ 14353 | propionic acid ethanol | 2.4 3.3 |

What is claimed is:

1. A process for producing pyruvic acid by fermentation in an aqueous nutrient medium of a pyruvic acid producing mutant of the strain *Candida lipolytica* which requires methionine and thiamine for growth to accumulate pyruvic acid in the culture liquor, and recovering the pyruvic acid.

2. A process as in claim 1 wherein the yeast is *Candida lipolytica* FERM P-2628.

3. A process as claimed in claim 1 wherein the medium contains pure methionine and thiamine.

4. A process as in claim 1 wherein the medium contains yeast extract or corn steep liquor as a source of methionine and thiamine.

5. A process as in claim 1 carried out at a temperature of 25° C to 35° C and a pH of 3 to 8.

* * * * *